(12) United States Patent
Ohno et al.

(10) Patent No.: US 6,489,523 B1
(45) Date of Patent: Dec. 3, 2002

(54) PROCESS FOR PRODUCING HEXAFLUOROETHANE AND USE THEREOF

(75) Inventors: Hiromoto Ohno, Kawasaki (JP); Kazunari Kaga, Kawasaki (JP); Toshio Ohi, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/030,823

(22) PCT Filed: Jun. 20, 2001

(86) PCT No.: PCT/JP01/05256

§ 371 (c)(1),
(2), (4) Date: Jan. 14, 2002

(87) PCT Pub. No.: WO01/98240

PCT Pub. Date: Dec. 27, 2001

Related U.S. Application Data

(60) Provisional application No. 60/230,806, filed on Sep. 7, 2000.

(30) Foreign Application Priority Data

Jun. 21, 2000 (JP) ........................................ 2000-185654

(51) Int. Cl.⁷ .......................... C07C 17/38; C07C 19/08; C07C 17/08

(52) U.S. Cl. ........................ 570/177; 570/134; 570/164; 570/165; 570/166; 570/187; 570/188; 570/169

(58) Field of Search ................................. 570/177, 164, 570/165, 166, 167, 168, 169, 134

(56) References Cited

U.S. PATENT DOCUMENTS 5,523,499 A * 6/1996 Corbin et al. ............... 570/164

* cited by examiner

*Primary Examiner*—Alan Siegel
(74) *Attorney, Agent, or Firm*—Sughrue Mion, PLLC

(57) ABSTRACT

The present invention intends to provide a process for producing $CF_3CF_3$ with good profitability using $CF_3CHF_2$ containing a compound having chlorine atom within the molecule, and use thereof.

In the process of the present invention, a gas mixture containing $CF_3CHF_2$ and a compound having chlorine atom within the molecule is reacted with hydrogen fluoride in the presence of a fluorination catalyst, thereby converting $CClF_2CF_3$ as a main impurity into $CF_3CF_3$, and $CF_3CHF_2$ containing $CF_3CF_3$ is reacted with fluorine gas in the gaseous phase in the presence of a diluting gas.

19 Claims, No Drawings

PROCESS FOR PRODUCING HEXAFLUOROETHANE AND USE THEREOF

CROSS REFERENCE TO RELATED APPLICATION

This application is a 371 of PCT/JP01/05256 filed Jun. 20, 2001, which claims benefit of an application filed under 35 U.S.C. §111(a) claiming benefit pursuant to 35 U.S.C. §119(e)(1) of the filing date of Provisional Application No. 60/230,806 filed on Sep. 7, 2000, pursuant to 35 U.S.C. §111(b).

DETAILED DESCRIPTION OF THE INVENTION

1. Technical Field of the Invention

The present invention relates to a process for producing hexafluoroethane, comprising a step of reacting a gas mixture containing pentafluoroethane and a compound having chlorine atom with hydrogen fluoride in the gaseous phase in the presence of a fluorination catalyst to fluorinate the compound having chlorine atom and a step of reacting the gas mixture containing pentafluoroethane and the fluorinated compound with fluorine gas in the gaseous phase in the presence of a diluting gas, and also relates to the use thereof.

2. Background Art

Pentafluoroethane (hereinafter referred to as "$CF_3CHF_2$") is used, for example, as a refrigerant for low-temperature use or a starting material for the production of hexafluoroethane (hereinafter referred to as "$CF_3CF_3$").

For the production of $CF_3CHF_2$, for example, the following methods have been heretofore known:

(1) a method of fluorinating perchloroethylene ($CCl_2=CCl_2$) or a fluoride thereof with hydrogen fluoride (see, JP-A-5-97724 (the term "JP-A" as used herein means an "unexamined published Japanese patent application"), JP-A-6-506221, JP-A-7-76534, JP-A-7-118182, JP-A-8-268932 and JP-A-9-511515), (2) a method of performing hydrogenolysis of chloropentafluoroethane ($CClF_2CF_3$), and (3) a method of reacting a fluorine gas with a halogen-containing ethylene (see, JP-A-1-38034).

When these methods for producing $CF_3CHF_2$ are used, the objective $CF_3CHF_2$ contains a compound having chlorine atom within the molecule as main impurities. The compound having chlorine atom within the molecule includes a compound having one carbon atom within the molecule, such as chloromethane, chlorodifluoromethane and chlorotrifluoromethane, a compound having two carbon atoms within the molecule, such as chloropentafluoroethane, dichlorotetrafluoroethane, chlorotetrafluoroethane and chlorotrifluoroethane, and an unsaturated compound such as chlorotrifluoroethylene.

In the case of producing $CF_3CF_3$ by a direct fluorination reaction of reacting $CF_3CHF_2$ with a fluorine gas ($F_2$), if $CF_3CHF_2$ contains the compound having chlorine atom within the molecule, chlorine, hydrogen chloride, chlorine fluoride or different kinds of chlorofluorocarbons are generated in the reaction with fluorine gas. Even when hydrofluorocarbons (HFC) or perfluorocarbons (PFC) are contained in $CF_3CHF_2$, there arises no particular problem, however, for example, chloromethane ($CH_3Cl$) or chlorodifluoromethane ($CHClF_2$) reacts with fluorine gas to produce chlorotrifluoromethane ($CClF_3$). The objective $CF_3CF_3$ and chlorotrifluoromethane form an azeotropic composition, therefore, $CClF_3$ is difficult to remove even by performing distillation, adsorption for purification, or the like. Accordingly, in the case of reacting $CF_3CHF_2$ with a fluorine gas to produce $CF_3CF_3$, the amount of the compound having chlorine atom within the molecule contained in $CF_3CHF_2$ should be reduced as much as possible.

According to conventional production methods for $CF_3CHF_2$, the total amount of the compound having chlorine atom within the molecule is sometimes as high as about 1 vol %. Therefore, a distillation operation is repeated for removing these compounds contained in $CF_3CHF_2$ and elevating the purity of $CF_3CHF_2$, however, this has such a problem that the distillation cost increases, the distillation loss is caused, the profitability is bad and some compounds having chlorine atom within the molecule form an azeotropic mixture or an azeotrope-like mixture with $CF_3CHF_2$ and are very difficult to remove only by the distillation operation. In particular, chloropentafluoroethane (hereinafter referred to as "$CClF_2CF_3$") is usually contained in $CF_3CHF_2$ in a concentration of thousands of ppm or more but since an azeotropic mixture is formed by $CF_3CHF_2$ and $CClF_2CF_3$, the separation is hardly attained by distillation which is a commonly used separation and purification method.

For separating $CClF_2CF_3$ contained in $CF_3CHF_2$, various methods have been proposed, for example, (1) a method of adding a third component to a mixture of $CF_3CHF_2$ and $CClF_2CF_3$ and performing the extractive distillation (see, JP-A-6-510980, JP-A-7-133240, JP-A-7-258123, JP-A-8-3082, JP-A-8-143486 and JP-A-10-513190), (2) a method of removing $CClF_2CF_3$ contained in $CF_3CHF_2$ using an adsorbent (see, JP-A-6-92879 and JP-W-8-508479 (the term "JP-W" as used herein means an "unexamined published international patent application")), and (3) a method of converting $CClF_2CF_3$ contained in $CF_3CHF_2$ into $CF_3CHF_2$ in the presence of a hydrogenation catalyst (see, JP-A-7-509238, JP-A-8-40949, JP-A-8-301801 and JP-A-10-87525).

However, these methods have a problem, that is, the method of (1) requires a step of recovering the third component from the mixture of $CClF_2CF_3$ and the third component, the method of (2) requires a step of regenerating the adsorbent, and the method of (3) suffers from reduction in the catalytic life due to hydrogen chloride produced.

Problems to be Solved by the Invention

The present invention has been made under these circumstances and the object of the present invention is to provide a method for producing $CF_3CF_3$ with good profitability using a gas mixture containing $CF_3CHF_2$ and a compound having chlorine atom within the molecule in the method for producing $CF_3CF_3$ which is used as an etching or cleaning gas in the process of producing a semiconductor device, and also provide a use thereof.

Means to Solve the Problems

As a result of extensive investigations to solve the above-described problems, the present inventors have found that in the method for producing $CF_3CF_3$, when a gas mixture containing $CF_3CHF_2$ and a compound having chlorine atom within the molecule as impurities is reacted with hydrogen fluoride in the presence of a fluorination catalyst to convert $CClF_2CF_3$ which is contained in the gas mixture, into $CF_3CF_3$ and then performing a direct fluorination reaction of reacting the resulting gas mixture containing $CF_3CHF_2$ and $CF_3CF_3$ with a fluorine gas in the gaseous phase in the presence of a diluting gas, the above-described problems can be solved. The present invention has been accomplished based on this finding. The present invention provides a process for producing $CF_3CF_3$ and use thereof, described in [1] to [19] below.

[1] A process for producing hexafluoroethane, comprising the following two steps:
(1) a step of reacting a gas mixture containing pentafluoroethane and a compound having chlorine atom with hydrogen fluoride in the gaseous phase in the presence of a fluorination catalyst to fluorinate the compound having chlorine atom; and
(2) a step of reacting the gas mixture containing pentafluoroethane and the fluorinated compound obtained in the step (1) with a fluorine gas in the gaseous phase in the presence of a diluting gas.

[2] The process for producing hexafluoroethane as described in [1], wherein the compound having chlorine atom is at least one compound selected from the group consisting of chloromethane, chlorotrifluoromethane, chloropentafluoroethane, dichlorotetrafluoroethane, chlorotetrafluoroethane, chlorotrifluoroethane and chlorotrifluoroethylene.

[3] The process for producing hexafluoroethane as described in [1] or [2], wherein the total amount of the compound having chlorine atom contained in the gas mixture of the step (1) is 1 vol % or less.

[4] The process for producing hexafluoroethane as described in [1] or [2], wherein the total amount of the compound having chlorine atom contained in the gas mixture of the step (1) is 0.5 vol % or less.

[5] The process for producing hexafluoroethane as described in any one of [1j to [4], wherein in the step (1), the fluorination catalyst is a bulk catalyst obtained by adding indium to an oxide of chromium.

[6] The process for producing hexafluoroethane as described in any one of [1] to [5], wherein in the step (1), the temperature at the reaction with hydrogen fluoride in the presence of a fluorination catalyst is in the range of 150 to 480° C.

[7] The process for producing hexafluoroethane as described in any one of [1] to [6], wherein in the step (1), the molar ratio of hydrogen fluoride/organic substance contained in the gas mixture is in the range of 0.5 to 5.

[8] The process for producing hexafluoroethane as described in any one of [1] to [7], wherein a step of removing an acid content containing hydrogen chloride produced is conducted before the step (2).

[9] The process for producing hexafluoroethane as described in any one of [1] to [8], wherein a step of separating chlorotetrafluoroethane and/or chlorotrifluoroethane, and returning the chlorotetrafluoroethane and/or chlorotrifluoroethane separated to the step (1) is conducted before the step (2).

[10] The process for producing hexafluoroethane as described in any one of [1] to [9], wherein in the step (2), the total amount of the compound having chlorine atom contained in the gas mixture is 0.02 vol % or less.

[11] The process for producing hexafluoroethane as described in any one of [1] to [10], wherein in the step (2), the fluorinated compound contained in the gas mixture is mainly composed of hexafluoroethane.

[12] The process for producing hexafluoroethane as described in any one of [1] to [11], wherein in the step (2), the diluting gas is a gas containing at least one selected from the group consisting of tetrafluoromethane, hexafluoroethane, octafluoropropane and hydrogen fluoride.

[13] The process for producing hexafluoroethane as described in any one of [1] to [12], wherein in the step (2), the diluting gas is a gas rich in hydrogen fluoride.

[14] The process for producing hexafluoroethane as described in any one of [1] to [13], wherein in the step (2), the temperature at the reaction of gas mixture containing the fluorinated compound with fluorine gas is in the range of 250 to 500° C.

[15] The process for producing hexafluoroethane as described in any one of [1] to [14], wherein in the step (2), the temperature at the reaction of gas mixture containing the fluorinated compound with fluorine gas is in the range of 350 to 450° C.

[16] A hexafluoroethane product comprising hexafluoroethane having a purity of 99.9997 vol % or more.

[17] The hexafluoroethane product as described in [16], wherein the content of the compound having chlorine atom is 1 volppm or less and the content of the pentafluoroethane is 1 volppm or less.

[18] An etching gas comprising the hexafluoroethane product described in [16] or [17].

[19] A cleaning gas comprising the hexafluoroethane product described in [16] or [17].

In summary, the present invention provides "a process for producing $CF_3CF_3$, comprising a step of reacting a gas mixture containing $CF_3CHF_2$ and a compound having chlorine atom with hydrogen fluoride in the gaseous phase in the presence of a fluorination catalyst to fluorinate the compound having chlorine atom and a step of reacting a gas mixture containing $CF_3CHF_2$ and the fluorinated compound obtained by the above-described step with a fluorine gas in the gaseous phase in the presence of a diluting gas", "an $CF_3CF_3$ product comprising $CF_3CF_3$ having a purity of 99.9997 vol % or more", "an etching gas comprising the above-described $CF_3CF_3$ product" and "a cleaning gas comprising the above-described $CF_3CF_3$ product".

MODE FOR CARRY OUT THE INVENTION

The production process for $CF_3CF_3$ and use thereof according to the present invention are described in detail below.

As described above, $CF_3CHF_2$ for use in the present invention is generally produced by fluorinating perchloroethylene ($CCl_2=CCl_2$) or a fluoride thereof with hydrogen fluoride (HF), and $CF_3CHF_2$ contains a compound having chlorine atom derived from the starting material, such as chloromethane, chlorodifluoromethane, chlorotrifluoromethane, chloropentafluoroethane, dichlorotetrafluoroethane, chlorotetrafluoroethane and chlorotrifluoroethane. In order to purify $CF_3CHF_2$ containing these compounds to a high purity, known methods by a distillation operation are employed, however, these methods have such a problem that these are not economical since the compound and $CF_3CHF_2$ form an azeotropic mixture or an azeotrope-like mixture, the purification by separation is very difficult, the number of stages of the distillation tower or the number of the distillation towers must be increased, and the cost for equipment or energy increases.

In the present invention, the compound having chlorine atom contained in $CF_3CHF_2$ as impurities is fluorinated with hydrogen fluoride at an elevated temperature in the presence of a fluorination catalyst and thereby converted into hydrofluorocarbon (HFC) or perfluorocarbon (PFC). For example, in fluorinating $CClF_2CF_3$ or chlorotetrafluoroethane contained as impurities in $CF_3CHF_2$ using hydrogen fluoride, a reaction shown by the following formula (1) or (2) takes place:

$$CF_3CClF_2 + HF \rightarrow CF_3CF_3 + HCl \quad (1)$$

$$CF_3CHClF + HF \rightarrow CF_3CHF_2 + HCl \quad (2)$$

The product is HFC or PFC free of chlorine atom, and hydrogen chloride is produced as a by-product.

In the present specification, the gas mixture containing $CF_3CHF_2$ and the compound having chlorine atom is sometimes referred to as "starting gas mixture".

In this fluorination reaction, the compound which is converted into HFC or PFC is chloromethane, chlorodifluoromethane, chlorotrifluoromethane, chloropentafluoroethane, dichlorotetrafluoroethane, chlorotetrafluoroethane and chlorotrifluoroethane. These compounds are usually contained in $CF_3CHF_2$ in a total amount of thousands of ppm or more. When the starting gas mixture containing these compounds is reacted with a fluorine gas, the methane-type compounds are converted into $CClF_3$ and the ethane-type compounds are converted into $CClF_2CF_3$, therefore, $CF_3CF_3$ obtained after the reaction contains $CClF_3$ and $CClF_2CF_3$ as main impurities.

$CClF_2CF_3$ scarcely reacts with a fluorine gas at low temperatures. However, according to the investigations by the present inventors, for example, at a reaction temperature of 400° C., the amount of $CClF_3$ produced by the decomposition of $CClF_2CF_3$ is 1 ppm or less when the concentration of $CClF_2CF_3$ contained in the starting gas mixture is about 800 ppm or less, and about 2 ppm of $CClF_3$ is produced when the concentration of $CClF_2CF_3$ exceeds about 2,000 ppm. $CClF_3$ forms an azeotropic mixture with $CF_3CF_3$, therefore, even if the concentration is low, this compound is difficult to remove by an operation of distillation, adsorption for purification or the like. Accordingly, it is preferred that not only a compound which produces $CClF_3$ upon reaction with a fluorine gas is removed from $CF_3CHF_2$ as a starting material but also the $CClF_2CF_3$ content is reduced to a low concentration as much as possible.

The total amount of the compound having chlorine atom contained in the starting gas mixture for use in the present invention is preferably 1 vol % or less, more preferably 0.5 vol % or less, still more preferably 0.3 vol % or less. If the concentration of the compound having chlorine atom exceeds 1 vol %, the reaction must be performed at a high temperature and the life of the fluorination catalyst is disadvantageously shortened, moreover, a side reaction proceeds at the same time and the productivity decreases.

The fluorination catalyst comprises at least one element selected from the group consisting of chromium, nickel, zinc, indium and garium, and may be a known catalyst such as supported catalyst or bulk catalyst.

In the case of the supported catalyst, carrier is preferably an alumina and/or partially fluorinated alumina, and supporting ratio is preferably 30 wt % or less. In the case of the bulk catalyst, particularly preferred is those containing chromium as main component, and having atomic ratio of nickel, zinc, indium and/or garium to chromium of 0.01 to 0.6. In the present invention, most preferred is a bulk catalyst obtained by adding indium to an oxide of chromium.

In the step of fluorinating the compound having chlorine atom, the reaction temperature is preferably from 150 to 480° C. If the reaction temperature exceeds 480° C., the reaction is adversely affected, for example, the catalyst deteriorates or a side reaction proceeds, and this is not preferred. Although it may vary depending on the concentration of the compound contained in the starting gas mixture, a preferred reaction temperature can be selected according to the kind of the compound. For example, in the reaction of $CClF_2CF_3$ shown in formula (1), the reaction temperature is preferably 400° C. or more, and in the reaction of $CF_3CHClF$ shown by formula (2), the reaction temperature is preferably 300° C. or more.

In the case of a reaction of chlorodifluoromethane ($CHClF_2$) with hydrogen fluoride, a reaction shown by the following formula (3) takes place:

$$CHClF_2 + HF \rightarrow CHF_3 + HCl \quad (3)$$

In this reaction, the reaction temperature is preferably 150° C. or more and if the reaction temperature exceeds 400° C. or more, a reverse reaction disadvantageously proceeds.

In the step of fluorinating a compound having chlorine atom, the reaction temperature sometimes varies depending on the kind of the compound as described above. Accordingly, in the case where a plurality of compounds are contained and these are different from each other in the optimal reaction temperature region or the concentration of each compound is high, two or more units of reactors are preferably used, though one unit of a reactor is usually sufficient.

The amount of HF used is, in terms of the molar ratio to the organic substance of the starting gas mixture containing $CF_3CHF_2$ (HF/organic substance), suitably from 0.5 to 5, preferably from 0.5 to 2. If the molar ratio is less than 0.5, the reaction is hard to proceed, whereas if it exceeds 5, a large reactor is necessary and this is not profitable.

Furthermore, in the step of fluorinating a compound having chlorine atom, the reaction pressure is preferably from atmospheric pressure to 1.5 MPa. If it exceeds 1.5 MPa, the apparatus is disadvantageously required to have pressure resistance or the like.

In the present invention, the reaction with hydrogen fluoride is performed in the presence of a fluorination catalyst using the above-described reaction conditions, and then $CF_3CHF_2$, chlorine atom-free impurities mainly comprising HFC or PFC, and hydrogen chloride as a by-product are contained in the reaction product. In the case of $CF_3CHF_2$, as the reaction temperature becomes higher, a side reaction with hydrogen chloride more proceeds as shown in the following formula (4):

$$CF_3CHF_2 + HCl \rightarrow CF_3CHClF + HF \quad (4)$$

In the case of containing 1,1,1,2-tetrafluoroethane, a side reaction with hydrogen chloride more proceeds as shown in the following formula (5):

$$CF_3CH_2F + HCl \rightarrow CF_3CH_2Cl + HF \quad (5)$$

Therefore, after the fluorination step of (1), the acid content containing hydrogen chloride produced is preferably removed.

The acid content is removed so as to remove unreacted hydrogen fluoride (excess hydrogen fluoride) and hydrogen chloride as a by-product. Hydrogen fluoride brings about no adverse effect in the direct fluorination reaction step but hydrogen chloride is preferably removed because this product sometimes causes an adverse effect such as production of a chlorine-containing compound or chlorine fluoride as shown in the formula (4) or (5). The step of removing the acid content is performed before the direct fluorination reaction step. Examples of the method for removing the acid content includes:

(1) in the case of containing a large amount of unreacted hydrogen fluoride, a method of introducing an effluent containing the acid content into a distillation tower, extracting hydrogen chloride from the top and extracting organic substance and hydrogen fluoride from the bottom, (2) a method of contacting the hydrogen chloride produced and unreacted hydrogen fluoride with a purifying agent, and (3) a method of washing the acid content with water or alkali water.

In the present invention, the method for removing the acid content is not particularly limited and, for example, the method of (3) may be used. The alkali used therein may be an aqueous sodium hydroxide solution, an aqueous potassium hydroxide solution or the like. The absorbed hydrogen fluoride may be recovered and reused, and the gas passed through the washing solution is dehydrated using a dehydrating agent such as zeolite.

The gas mainly comprising $CF_3CHF_2$ passed through the acid content-removing step sometimes contains as impurities HCFC or CFC which is not completely fluorinated by the reaction with hydrogen fluoride, and in such a case, HCFC or CFC is preferably removed by distilling before the direct fluorination reaction step.

$CF_3CHF_2$ and main compounds which may be contained in $CF_3CHF_2$ are shown, together with respective boiling points in Table 1.

TABLE 1

| Compound Name | Structural Formula | Boiling Point (° C.) |
| --- | --- | --- |
| Tetrafluoromethane | $CF_4$ | −128 |
| Trifluoromethane | $CHF_3$ | −84 |
| Hexafluoroethane | $CF_3CF_3$ | −78.1 |
| Pentafluoroethane | $CF_3CHF_2$ | −48.5 |
| Chloropentafluoroethane | $CF_3CClF_2$ | −38.7 |
| 2-Chloro-1,1,1,2-tetrafluoroethane | $CF_3CHClF$ | −12 |
| 2-Chloro-1,1,1-trifluoroethane | $CF_3CH_2Cl$ | 6.1 |

The gas mainly comprising $CF_3CHF_2$ is introduced into a distillation tower, then $CF_4$, $CHF_3$, $CF_3CF_3$, $CF_3CHF_2$ and $CClF_2CF_3$ as the low boiling fraction are extracted from the top of the distillation tower, and $CF_3CHClF$ and $CF_3CH_2Cl$ as the high boiling fraction are extracted from the bottom. The high boiling fraction extracted from the bottom is circulated into the reaction with hydrogen fluoride of the step (1). Here, the total amount of the compound having chlorine atom, which is contained in the distillate mainly comprising $CF_3CHF_2$ extracted from the top, is preferably 0.02 vol % or less. The distillate mainly comprising $CF_3CHF_2$ is used as a starting material in the direct fluorination reaction with fluorine gas.

The step (2) of reacting the gas mainly comprising $CF_3CHF_2$ with fluorine gas is described below.

The step (2) is performed in the presence of a diluting gas and the gas mainly comprising $CF_3CHF_2$ is set to a concentration lower than the explosion range. Specifically, the $CF_3CHF_2$ concentration at the reactor inlet is preferably set to about 6 mol % or less. The diluting gas is a gas containing at least one selected from the group consisting of tetrafluoromethane, hexafluoroethane, octafluoropropane and hydrogen fluoride, preferably a diluting gas rich in hydrogen fluoride.

The amount of fluorine gas used is, in terms of the molar ratio to $CF_3CHF_2$ ($F_2/CF_3CHF_2$), suitably in the range of 0.5 to 2, preferably in the range of 0.9 to 1.3. The reaction temperature is in the range of 250 to 500° C., preferably in the range of 350 to 450° C. If the reaction temperature exceeds 500° C., the objective $CF_3CF_3$ is disadvantageously cleaved to produce $CF_4$ and in the case of containing $CClF_2CF_3$ as an impurity, $CClF_3$ is disadvantageously produced due to cleavage of $CClF_2CF_3$, whereas if it is less than 250° C., the reaction slowly proceeds and this is not preferred.

The method for purifying the gas distilled out from the reaction step of (2) is not particularly limited. The remaining unreacted fluorine gas may be removed by adding, for example, trifluoromethane as HFC and then the residue is distilled to separate, for example, hydrogen fluoride and organic substance. The separated hydrogen fluoride is reused as the diluting gas in the direct fluorination reaction of the step (2) but may also be used as a starting material in the fluorination reaction of (1). The composition of the organic substance separated greatly differs depending on the diluting gas used for the reaction and in the case of using a gas rich in hydrogen fluoride or in the objective $CF_3CF_3$, the organic substance obtained contains $CF_3CF_3$ as a main component. In the case of using tetrafluoromethane or octafluoropropane as the diluting gas, the gas is purified by again performing distillation. In either case, high-purity $CF_3CF_3$ can be obtained by repeatedly performing the distillation operation according to the compositional ratio of the organic substance obtained.

In the distillation for purification of the organic substance, although it may vary depending on the compositional ratio, for example, an inert gas and $CF_4$ as the low boiling fraction are extracted from the top of the first distillation tower and the gas mainly comprising $CF_3CF_3$ is extracted from the bottom and introduced into the second distillation tower. Then, an inert gas and trifluoromethane as the low boiling fraction are extracted from the top of the second distillation tower and the gas mainly comprising $CF_3CF_3$ is extracted from the bottom and introduced into the third distillation tower to extract high-purity $CF_3CF_3$ from the top, thereby performing the purification. The gas containing $CClF_2CF_3$ collected from the bottom in the third distillation may be circulated into the reaction step with hydrogen fluoride of (1).

The thus-purified $CF_3CF_3$ contains almost no impurities and high-purity $CF_3CF_3$ can be obtained. The purity thereof is 99.9997 vol % or more, and 1 volppm or less of the compound having chlorine atom and 1 volppm or less of pentafluoroethane are contained as impurities.

As the analysis method of $CF_3CF_3$ having a purity of 99.9997 vol % or more, gas chromatography (GC) using TCD method, FID method (each including the precut method) or ECD method, or an instrument such as gas chromatography mass spectrometer (GC-MS) may be used.

Use of $CF_3CF_3$ obtained by the production process of the present invention is described below.

The high-purity $CF_3CF_3$ can be used as an etching gas at the etching step in the process of manufacturing a semiconductor device and also can be used as a cleaning gas at the cleaning step in the process of manufacturing a semiconductor device.

In the process of manufacturing a semiconductor device such as LSI and TFT, a thin or thick film is formed using CVD, sputtering or vapor deposition, and the film is etched to form a circuit pattern. In the apparatus for forming a thin or thick film, cleaning for removing unnecessary deposits accumulated on the inner wall of the apparatus, jigs and the like is performed, because the produced unnecessary deposits cause generation of particles and must be removed on occasions so as to produce a film having good quality.

The etching process using $CF_3CF_3$ can be performed under various dry etching conditions such as plasma etching and microwave etching, and $CF_3CF_3$ may be used by mixing it with an inert gas such as He, $N_2$ and Ar or with a gas such as HCl, $O_2$ and $H_2$ at an appropriate ratio.

EXAMPLES

The present invention is described in greater detail below by referring to the Examples and Comparative Examples, however, the present invention is not limited to these Examples.

Raw Material Example 1

In the presence of a fluorination catalyst, tetrachloroethylene ($CCl_2$=$CCl_2$) was reacted with HF at a reaction pressure of 0.4 MPa, a reaction temperature of 300° C. and a molar ratio HF/tetrachloroethylene of 4 (first reaction) and then, the reaction was further continued at a reaction pressure of 0.4 MPa, a reaction temperature of 330° C. and a molar ratio HF/intermediate ($CF_3CHCl_2$+$CF_3CHClF$) of 4 (second reaction). After the reaction, the removal of acid content and a distillation operation were performed by a conventional method, and the distillate was analyzed by gas chromatography, as a result, crude $CF_3CHF_2$ (Raw Material 1 of $CF_3CHF_2$) having a composition shown in Table 2 was obtained.

TABLE 2

| Compound | Purity (vol %) |
|---|---|
| $CF_3CHF_2$ | 99.4513 |
| $CH_3Cl$ | 0.0011 |
| $CHClF_2$ | 0.0008 |
| $CHF_3$ | 0.0224 |
| $CClF_3$ | 0.0005 |
| $CF_3CClF_2$ | 0.5216 |
| $CF_3CHClF$ | 0.0008 |
| $CF_3CCl_2F$ | 0.0009 |
| $CF_3CH_2Cl$ | 0.0006 |

Raw Material Example 2

Raw Material 1 of $CF_3CHF_2$ obtained by the above-described method was repeatedly distilled by a conventional method, and the distillate was analyzed by gas chromatography, as a result, crude $CF_3CHF_2$ (Raw Material 2 of $CF_3CHF_2$) having a composition shown in Table 3 was obtained.

TABLE 3

| Compound | Purity (vol %) |
|---|---|
| $CF_3CHF_2$ | 99.8000 |
| $CHClF_2$ | 0.0002 |
| $CHF_3$ | 0.0038 |
| $CF_3CClF_2$ | 0.1960 |

Catalyst Example 1

Into a 10 L-volume container containing 0.6 L of pure water, a solution containing 452 g of $Cr(NO_3)_3 \cdot 9H_2O$ dissolved in 1.2 L of pure water and 0.31 L of 28% aqueous ammonia were added dropwise over about 1 hour while stirring under the control to give a reaction solution having a pH of 7.5 to 8.5. The resulting hydroxide slurry was filtrated, thoroughly washed with pure water and then dried at 120° C. The thus-obtained solid was pulverized, mixed with graphite and then pelletized by a tabletting machine. The pellets obtained were calcined at 400° C. for 4 hours in a nitrogen stream to obtain a catalyst precursor. This catalyst precursor was filled into an Inconel-made reactor and subsequently subjected to a fluorination treatment (activation of catalyst) at an atmospheric pressure and 350° C. in an atmosphere of HF diluted with nitrogen, then in a 100% HF stream, and further at 450° C. in an atmosphere of HF diluted with nitrogen to prepare a catalyst.

Catalyst Example 2

Into a 10 L-volume container containing 0.6 L of pure water, a solution containing 452 g of $Cr(NO_3)_3 \cdot 9H_2O$ and 42 g of $In(NO_3)_3 \cdot nH_2O$ (n is about 5) dissolved in 1.2 L of pure water, and 0.31 L of 28% aqueous ammonia were added dropwise over about 1 hour while stirring under the control of respective flow rates of two aqueous solutions to give a reaction solution having a pH of 7.5 to 8.5. The resulting hydroxide slurry was filtrated, thoroughly washed with pure water and then dried at 120° C. for 12 hours. The thus-obtained solid was pulverized, mixed with graphite and then pelletized by a tabletting machine. The pellets obtained were calcined at 400° C. for 4 hours in a nitrogen stream to obtain a catalyst precursor. Into an Inconel-made reactor, the catalyst precursor was filled and subsequently subjected to a fluorination treatment (activation of catalyst) in the same manner as in Catalyst Example 1 to prepare a catalyst.

Example 1

Step (1)

Into an Inconel 600-type reactor having an inner diameter of 1 inch and a length of 1 m, 150 ml of the catalyst prepared in [Catalyst Example 1] was filled, and the temperature was elevated to 440° C. while passing nitrogen. Thereto, hydrogen fluoride was fed at 3.5 NL/hr and then Raw Material 1 of $CF_3CHF_2$ obtained in [Raw Material Example 1] was fed at 3.5 NL/hr. The feeding of nitrogen gas was stopped and the reaction was initiated. After 2 hours, the exhaust gas was washed with an aqueous potassium hydroxide solution to remove the acid content and thereafter, the gas composition was analyzed by gas chromatography, as a result, a gas having a composition shown in Table 4 was obtained.

TABLE 4

| Compound | Purity (vol %) |
|---|---|
| $CF_3CHF_2$ | 99.3273 |
| $CF_4$ | 0.0113 |
| $CHF_3$ | 0.0215 |
| $CF_3CF_3$ | 0.6120 |
| $CF_3CClF_2$ | 0.0156 |
| $CF_3CHClF$ | 0.0112 |
| $CF_3CH_2Cl$ | 0.0011 |

Example 2

Step (1)

A reaction and an analysis were performed under the same conditions through the same operations as in Example 1 except for filling 150 ml of the catalyst prepared in Catalyst Example 2 as the catalyst. The analysis results are shown in Table 5.

TABLE 5

| Compound | Purity (vol %) |
|---|---|
| $CF_3CHF_2$ | 99.2732 |
| $CF_4$ | 0.0170 |

TABLE 5-continued

| Compound | Purity (vol %) |
|---|---|
| $CHF_3$ | 0.0212 |
| $CF_3CF_3$ | 0.6720 |
| $CF_3CClF_2$ | 0.0068 |
| $CF_3CHClF$ | 0.0098 |
| $CF_3CH_2Cl$ | 0.0015 |

As is apparent from the analysis results shown in Table 5, when a fluorination catalyst obtained by adding indium to chromium is used, the conversion ratio of $CClF_2CF_3$ to $CF_3CF_3$ is improved.

Example 3

Step (1)

A reaction and an analysis were performed under the same conditions through the same operations as in Example 1 except for changing the reaction temperature to 300° C. The analysis results are shown in Table 6.

TABLE 6

| Compound | Purity (vol %) |
|---|---|
| $CF_3CHF_2$ | 99.4314 |
| $CF_4$ | 0.0023 |
| $CHF_3$ | 0.0221 |
| $CF_3CF_3$ | 0.0387 |
| $CF_3CClF_2$ | 0.4829 |
| $CF_3CHClF$ | 0.0014 |
| $CF_3CH_2Cl$ | 0.0005 |

Example 4

Step (1)

A reaction and an analysis were performed under the same conditions through the same operations as in Example 1 except for changing the reaction temperature to 500° C. The analysis results are shown in Table 7.

TABLE 7

| Compound | Purity (vol %) |
|---|---|
| $CF_3CHF_2$ | 99.1948 |
| $CF_4$ | 0.1488 |
| $CHF_3$ | 0.0168 |
| $CF_3CF_3$ | 0.5880 |
| $CHClF_2$ | 0.0069 |
| $CF_3CClF_2$ | 0.0148 |
| $CF_3CHClF$ | 0.0256 |
| $CF_3CCl_2F$ | 0.0021 |
| $CF_3CH_2Cl$ | 0.0022 |

Example 5

Step (1)+Step (2)

Into an Inconel 600-type reactor having an inner diameter of 1 inch and a length of 2 m, 150 ml of the catalyst prepared in [Catalyst Example 2] was filled, and the temperature was elevated to 430° C. while passing nitrogen. Thereto, hydrogen fluoride was fed at 5.0 NL/hr and then Raw Material 2 of $CF_3CHF_2$ obtained in [Raw Material Example 2] was fed at 8.0 NL/hr. Subsequently, the feeding of nitrogen gas was stopped and 2 hours after the initiation of the reaction, the exhaust gas was washed with aqueous potassium hydroxide solution to remove the acid content. The resulting gas composition was analyzed by gas chromatography, as a result, a gas having the composition shown in Table 8 was obtained.

TABLE 8

| Compound | Purity (vol %) |
|---|---|
| $CF_3CHF_2$ | 99.7922 |
| $CF_4$ | 0.0018 |
| $CHF_3$ | 0.0036 |
| $CF_3CF_3$ | 0.1980 |
| $CF_3CClF_2$ | 0.0008 |
| $CF_3CHClF$ | 0.0036 |

The gas having the composition shown in Table 8 after the removal of the acid content was collected under cooling and purified by distillation according to a conventional method. The gas obtained after the purification was analyzed and the results are shown in Table 9.

TABLE 9

| Compound | Purity (vol %) |
|---|---|
| $CF_3CHF_2$ | 99.7950 |
| $CF_4$ | 0.0019 |
| $CHF_3$ | 0.0035 |
| $CF_3CF_3$ | 0.1988 |
| $CF_3CClF_2$ | 0.0008 |

As is apparent from the analysis results shown in Table 9, by performing distillation, chlorotetrafluoroethane can be mostly removed.

Using the gas mainly comprising $CF_3CHF_2$ after the purification by distillation obtained above, a direct fluorination reaction with fluorine gas was performed.

An Inconel 600-type reactor having an inner diameter of 20.6 mmφ and a length of 500 mm (using a heating system by an electric heater; the reactor had been subjected to a passivation treatment with fluorine gas at a temperature of 500° C.) was heated to a temperature of 420° C. while passing nitrogen gas at 30 NL/hr.

Then, hydrogen fluoride was fed at 50 NL/hr, and into one gas flow diverged from the diluting gas, the gas mainly comprising $CF_3CHF_2$ was fed at 3.5 NL/hr. Thereafter, fluorine gas was similarly fed at 3.85 NL/h to another gas flow diverged from the diluting gas to perform a reaction. After 3 hours, the reaction product gas was washed with an aqueous potassium hydroxide solution and an aqueous potassium iodide solution to remove hydrogen fluoride and unreacted fluorine gas. Subsequently, the gas composition was analyzed by gas chromatography. The analysis results are shown in Table 10.

TABLE 10

| Compound | Purity (vol %) |
|---|---|
| $CF_3CHF_2$ | 0.0001 |
| $CF_4$ | 0.0456 |
| $CF_3CF_3$ | 99.9536 |
| $CF_3CClF_2$ | 0.0007 |

The gas after the removal of the acid content was collected under cooling and purified by distillation.

The gas after the purification was analyzed by gas chromatography using TCD method, FID method, ECD method and GC-MS method, and the analysis results are shown in Table 11.

TABLE 11

| Compound | Purity (vol %) |
| --- | --- |
| $CF_3CHF_2$ | 0.9 vol ppm |
| $CF_4$ | <0.4 vol ppm |
| $SF_6$ | <0.4 vol ppm |
| $CF_3CClF_2$ | <0.1 vol ppm |
| $CF_3CF_3$ | 99.9998 vol % |

As is apparent from the analysis results shown in Table 11, $CF_3CF_3$ after the purification contains almost no other impurities, thus, high-purity $CF_3CF_3$ is obtained and the purity thereof is 99.9997 vol % or more.

Comparative Example 1

An Inconel 600-type reactor having an inner diameter of 20.6 mm$\phi$ and a length of 500 mm (using a heating system by an electric heater; the reactor had been subjected to a passivation treatment with fluorine gas at a temperature of 500° C.) was heated to a temperature of 420° C. while passing nitrogen gas at 30 NL/h.

Then, hydrogen fluoride was fed at 50 NL/hr, and into one gas flow diverged from the diluting gas, Raw Material 1 of $CF_3CHF_2$ obtained in (Raw Material Example 1] was fed at 3.5 NL/hr. Thereafter, fluorine gas was similarly fed at 3.85 NL/h into another gas flow diverged from the diluting gas to perform a reaction. After 3 hours, the reaction product gas was washed with an aqueous potassium hydroxide solution and an aqueous potassium iodide solution to remove hydrogen fluoride and unreacted fluorine gas. Subsequently, the gas composition was analyzed by gas chromatography. The analysis results are shown in Table 12.

TABLE 12

| Compound | Purity (vol %) |
| --- | --- |
| $CF_3CHF_2$ | 0.0003 |
| $CF_4$ | 0.0568 |
| $CClF_3$ | 0.0036 |
| $CF_3CF_3$ | 99.4160 |
| $CF_3CClF_2$ | 0.5233 |

As is apparent from the analysis results shown in Table 12, when $CF_3CHF_2$ containing a compound having chlorine atom within the molecule as impurities is reacted with fluorine gas, $CClF_3$ (chlorotrifluoromethane) which is a substance difficult to separate, is produced.

Then, the gas having the composition shown in Table 12 after the removal of the acid content was collected under cooling and purified by distillation. The gas obtained after the purification was analyzed and the results are shown in Table 13.

TABLE 13

| Compound | Purity (vol %) |
| --- | --- |
| $CF_3CHF_2$ | 0.0003 |
| $CF_4$ | <0.0001 |
| $CClF_3$ | 0.0036 |
| $CF_3CF_3$ | 99.9959 |
| $CF_3CClF_2$ | <0.0001 |

As is apparent from the analysis results shown in Table 13, $CClF_3$ is a compound hard to separate.

EFFECTS OF THE INVENTION

As described in the foregoings, by using starting gas mixture containing $CF_3CHF_2$ and a compound having chlorine atom, high-purity $CF_3CF_3$ can be produced, and the high-purity $CF_3CF_3$ produced according to the present invention can be used as an etching gas or a cleaning gas in the process of manufacturing a semiconductor device.

What is claimed is:

1. A process for producing hexafluoroethane, comprising the following two steps:
    (1) a step of reacting a gas mixture containing pentafluoroethane and a compound having chlorine atom with hydrogen fluoride in the gaseous phase in the presence of a fluorination catalyst to fluorinate said compound having chlorine atom; and
    (2) a step of reacting the gas mixture containing pentafluoroethane and the fluorinated compound obtained in said step (1) with a fluorine gas in the gaseous phase in the presence of a diluting gas.

2. The process for producing hexafluoroethane as claimed in claim 1, wherein said compound having chlorine atom is at least one compound selected from the group consisting of chloromethane, chlorotrifluoromethane, chloropentafluoroethane, dichlorotetrafluoroethane, chlorotetrafluoroethane, chlorotrifluoroethane and chlorotrifluoroethylene.

3. The process for producing hexafluoroethane as claimed in claim 1 or 2, wherein the total amount of the compound having chlorine atom contained in the gas mixture of the step (1) is 1 vol % or less.

4. The process for producing hexafluoroethane as claimed in claim 1 or 2, wherein the total amount of the compound having chlorine atom contained in the gas mixture of the step (1) is 0.5 vol % or less.

5. The process for producing hexafluoroethane as claimed in any one of claims 1 to 4, wherein in said step (1), the fluorination catalyst is a bulk catalyst obtained by adding indium to an oxide of chromium.

6. The process for producing hexafluoroethane as claimed in any one of claims 1 to 5, wherein in said step (1), the temperature at the reaction with hydrogen fluoride in the presence of a fluorination catalyst is in the range of 150 to 480° C.

7. The process for producing hexafluoroethane as claimed in any one of claims 1 to 6, wherein in said step (1), the molar ratio of hydrogen fluoride/organic substance contained in the gas mixture is in the range of 0.5 to 5.

8. The process for producing hexafluoroethane as claimed in any one of claims 1 to 7, wherein a step of removing an acid content containing hydrogen chloride produced is conducted before said step (2).

9. The process for producing hexafluoroethane as claimed in any one of claims 1 to 8, wherein a step of separating chlorotetrafluoroethane and/or chlorotrifluoroethane, and returning the chlorotetrafluoroethane and/or chlorotrifluoroethane separated to the step (1) is conducted before said step (2).

10. The process for producing hexafluoroethane as claimed in any one of claims 1 to 9, wherein in said step (2), the total amount of the compound having chlorine atom contained in the gas mixture is 0.02 vol % or less.

11. The process for producing hexafluoroethane as claimed in any one of claims 1 to 10, wherein in said step (2), the fluorinated compound contained in the gas mixture is mainly composed of hexafluoroethane.

12. The process for producing hexafluoroethane as claimed in any one of claims 1 to 11, wherein in said step (2), the diluting gas is a gas containing at least one selected from the group consisting of tetrafluoromethane, hexafluoroethane, octafluoropropane and hydrogen fluoride.

13. The process for producing hexafluoroethane as claimed in any one of claims 1 to 12, wherein in said step (2), the diluting gas is a gas rich in hydrogen fluoride.

14. The process for producing hexafluoroethane as claimed in any one of claims 1 to 13, wherein in said step (2), the temperature at the reaction of gas mixture containing the fluorinated compound with fluorine gas is in the range of 250 to 500° C.

15. The process for producing hexafluoroethane as claimed in any one of claims 1 to 14, wherein in said step (2), the temperature at the reaction of gas mixture containing the fluorinated compound with fluorine gas is in the range of 350 to 450° C.

16. A hexafluoroethane product comprising hexafluoroethane having a purity of 99.9997 vol % or more.

17. The hexafluoroethane product as claimed in claim 16, wherein the content of the compound having chlorine atom is 1 volppm or less and the content of the pentafluoroethane is 1 volppm or less.

18. An etching gas comprising the hexafluoroethane product described in claim 16 or 17.

19. A cleaning gas comprising the hexafluoroethane product described in claim 16 or 17.

* * * * *